United States Patent [19]
Chauvin et al.

[11] Patent Number: 5,874,638
[45] Date of Patent: Feb. 23, 1999

[54] PROCESS FOR HYDROFORMYLATION OF OLEFINIC COMPOUNDS

[75] Inventors: Yves Chauvin, Le Pecq; Hélène Olivier, Rueil Malmaison; Lothar Mussmann, Hanau-Wolfgang, all of France

[73] Assignee: Institut Francais du Petrole, France

[21] Appl. No.: 755,853

[22] Filed: Dec. 2, 1996

[30] Foreign Application Priority Data

Nov. 30, 1995 [FR] France .................................. 95 14147

[51] Int. Cl.⁶ .................................................. C07C 45/50
[52] U.S. Cl. ........................................... 568/454; 568/451
[58] Field of Search ...................................... 568/451, 454

[56] References Cited

U.S. PATENT DOCUMENTS

| | | | |
|---|---|---|---|
| 3,511,880 | 5/1970 | Booth | 260/604 |
| 3,832,391 | 8/1974 | Parshall | 260/497 |
| 4,451,679 | 5/1984 | Knifton et al. | 568/909 |
| 4,451,680 | 5/1984 | Knifton et al. | 568/451 |

FOREIGN PATENT DOCUMENTS 0 107 430   5/1984   European Pat. Off. .

*Primary Examiner*—Gary Geist
*Assistant Examiner*—Sreeni Padmanabhan
*Attorney, Agent, or Firm*—Millen, White, Zelano & Branigan, P.C.

[57] ABSTRACT

A hydroformylation process for unsaturated compounds such as monoolefins and diolefins is carried out in an ionic medium in which the catalytic species is dissolved, but in which the reaction products (aldehydes) formed are only slightly soluble or are insoluble. The ionic medium is liquid at a temperature below 90° C. and comprises at least one quaternary ammonium and/or phosphonium cation and at least one anion which is preferably selected from the group formed by tetrafluoroborate when the cation is ammonium, hexafluorophosphate, hexafluoroantimonate, hexafluoroarsenate, perfluoroalkylsulphonates, fluorosulphonate, bis-perfluoroalkylsulphonyl amides or dichlorocuprate, tetrachlorocuprate, tetrachloroaluminate, or trichlorozincate. At the end of the reaction, the organic phase is separated out and the polar phase containing the catalyst is used again.

28 Claims, No Drawings

PROCESS FOR HYDROFORMYLATION OF OLEFINIC COMPOUNDS

BACKGROUND OF THE INVENTION

The present invention concerns a novel hydroformylation process for olefinically unsaturated compounds using carbon monoxide and hydrogen, in which the catalytic system is a solution of at least one transition metal compound in a non-aqueous organic-inorganic ionic salt which is liquid at the reaction temperature, and in which the products of the hydroformylation reaction are slightly soluble or insoluble.

Hydroformylation of olefinic compounds is a reaction which is industrially very important. The majority of processes use catalysts which are dissolved in an organic phase constituted by the reactants, products and possibly excess ligands, even though there are difficulties in separating and recovering the catalyst, in particular when the latter is a noble metal such as rhodium.

One mode of resolving this problem has been described in French patent FR-A-2 314 910. It consists of carrying out hydroformylation in the presence of an aqueous solution containing a rhodium complex which is rendered water-soluble by the presence of a sulphonated phosphine ligand which is itself water-soluble, such as the sodium salt of trisulphonated triphenylphosphine. In this way, the organic phase containing the aldehydes is readily separated from the aqueous phase containing the catalyst. This technique has formed the subject matter of a considerable number of studies which were discussed in an article by W. A. Hermann in "Angewandte Chemie International" in 1993, volume 32, page 1524 ff. Despite the great industrial importance of this technique for propylene hydroformylation, such a two-phase system suffers from a lack of solubility in water of the olefins, leading to relatively low reaction rates which renders it inapplicable to long chain olefins.

United States patent US-A-3 565 823 describes a technique consisting of dispersing a transition metal compound in a salt of tin or germanium and a quaternary ammonium or phosphonium with formula $(R_1R_2R_3R_4Z)YX_3$ where $R_1$, $R_2$, $R_3$, $R_4$ are hydrocarbyl residues containing up to 18 carbon atoms, Z is nitrogen or phosphorous, Y is tin or germanium and X is a halogen, chlorine or bromine, the non-aqueous medium with ionic nature constituting a "molten salt". US-A-3 657 368 describes a process for hydrogenating olefins and US-A-3 919 271 describes a process for hydrogenating nitrites each using the above tin and germanium based composition. US-A-3 832 391 claims an olefin carbonylation process using the same composition.

European patent application EP-A-0 107 430 describes a hydroformylation process using a ruthenium catalyst dispersed in a quaternary phosphonium or ammonium salt or base with a melting point which is lower than the reaction temperature.

The anions of the salt used are the halides, nitrate, acetate, chromate or hydroxide. Tetrabutylphosphonium tetrafluoroborate can also be used.

All those salts have melting points of at least 100° C., more generally at least 120° C. The solid ruthenium catalyst is mixed with the solid salt and, in the presence of the reactant, is heated in its entirety to the reaction temperature at which the medium is liquid. The compositions described above have the disadvantage of having a relatively high melting point, the hydroformylation reaction thus being carried out at at least 90° C., or generally 160°–180° C. in EP-A-0 107 430.

SUMMARY OF THE INVENTION

We have now discovered that the advantages of operating with two phases can be exploited while avoiding the disadvantages linked to using water and to the use of high melting point compounds by dissolving catalytic compounds of transition metals from groups 8, 9 and 10, in particular compounds of cobalt, ruthenium, rhodium, iridium, palladium and platinum, known to catalyse hydroformylation, in organic-inorganic salts which are liquid at low temperatures. The salt acts as a solvent for the catalytic compound.

More precisely, the invention provides a process for liquid phase hydroformylation of olefinically unsaturated compounds in which the reaction is carried out in the presence of at least one organic-inorganic salt with general formula $Q^+A^-$, where $Q^+$ represents a quaternary ammonium and/or phosphonium, and $A^-$ represents an anion, said salt not containing tin or germanium, and said salt being liquid at a temperature below 90° C., and in the presence of at least one compound of a transition metal from groups 8, 9 and 10.

The liquid salts of the invention have general formula $Q^+A^-$, where $Q^+$ represents a quaternary ammonium and/or quaternary phosphonium and $A^-$ represents any anion which is known to be non-co-ordinating which can form a liquid salt at low temperatures, i.e., below 90° C., and preferably at most 85° C., more preferably below 50° C. Preferably, the ions are hexafluorophosphate, hexafluoroantimonate, hexafluoroarsenate, fluorosulphonate, tetrafluoroborate when $Q^+$ is ammonium, bis-perfluoroalkylsulphonyl amides (in particular methyl, butyl and nonyl), and perfluoroalkyl sulphonates (in particular methyl). Dichlorocuprate, tetrachloroborate, tetrachloroaluminate and trichlorozincate anions can also be used, but are not preferred. The quaternary ammonium and/or phosphonium compounds preferably have general formulae $NR^1R^2R^3R^{4+}$ and $PR^1R^2R^3R^{4+}$, or general formulae $R^1R^2N=CR^3R^{4+}$ and $R^1R^2P=CR^3R^{4+}$, where $R^1$, $R^2$, $R^3$ and $R^4$, which may be identical or different, are hydrogen with the exception of the $NH_4^+$ cation, and preferably a single substituent represents hydrogen, or hydrocarbyl residues containing 1 to 12 carbon atoms, for example saturated or unsaturated alkyls, cycloalkyls, or aryl or aralkyl aromatics containing 1 to 12 carbon atoms. The ammonium and/or phosphonium can also be derived from nitrogen-containing heterocycles or phosphorous-containing heterocycles containing 1, 2 or 3 nitrogen and/or phosphorous atoms, with general formulae:

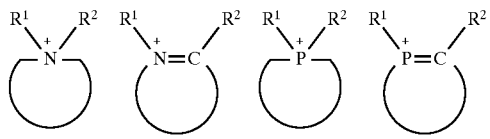

in which the cycles are constituted by 4 to 10 atoms, preferably 5 to 6 atoms, $R^1$ and $R^2$ being as defined above. The quaternary ammonium or phosphonium can also be a cation with formula:

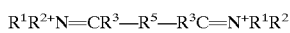

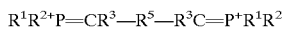

where $R^1$, $R^2$, $R^3$, which may be identical or different, are defined as above, and $R^5$ represents an alkylene or phenylene residue. Examples of groups $R^1$, $R^2$, $R^3$ and $R^4$ are the methyl, ethyl, propyl, isopropyl, butyl, secondary butyl, tertiary butyl, amyl, methylene, ethylidene, phenyl or benzyl radicals; $R^5$ may be a methylene, ethylene, propylene or phenylene group. The ammonium and/or phosphonium cation is preferably selected from the group formed by N-butylpyridinium, N-ethylpyridinium, 3-butyl-1

-methylimidazolium, diethylpyrazolium, 3-ethyl-1-methylimidazolium, pyridinium, trimethylphenylammonium, and tetrabutylphosphonium. Examples of salts which can be used in the process of the invention are N-butylpyridinium hexafluorophosphate, N-ethylpyridinium tetrafluoroborate, tetrabutylphosphonium tetrafluoroborate, 3-butyl-1-methylimidazolium hexafluoroantimonate, 3-butyl-1-methylimidazolium hexafluorophosphate, 3-butyl-1-methylimidazolium trifluoromethylsulphonate, pyridinium fluorosulphonate, and trimethylphenylammomium hexafluorophosphate. These salts can be used alone or as a mixture. They act as the solvent. Other examples are 3-butyl-1 -methylimidazolium dichlorocuprate, pyridinium tetrachloroborate, 3-butyl-1-methylimidazolium tetrachloroaluminate, and 3-butyl-1-methylimidazolium trichlorozincate.

The transition metal compounds are generally all compounds of transition metals from groups 8, 9 and 10, in particular those which are known to the skilled person for olefin hydroformylation. They can be used alone or as a mixture. They can be complexed or associated with an organic ligand. They can be used in the form of salts, as is preferred, but halides are not preferred. Among others, compounds of cobalt, rhodium, iridium, ruthenium, palladium and platinum can be used. Organic ligands such as tertiary phosphines, stibines and arsines, phosphites, and in particular arylphosphites can advantageously be associated with all these compounds. They can be mono- or bidentate. These ligands can carry at least one other function such as an amine, ammonium, alcohol, carboxylic acid or sulphonate on the heteroatom and/or on the carbon chain. Examples are triphenylphosphine, triphenylphosphite, trimethylphosphite, the sodium salt of monosulphonated triphenylphosphine, and the sodium salt of trisulphonated triphenylphosphine. The choice of transition metal catalytic compound is not critical. Examples are $HRh(CO)(PR_3)_3$, $HRh(CO)_2(PR_3)$, $HRh(CO)[P(OR)_3]_3$, $Rh(acac)(CO)_2$, (acac represents acetylaccetonate), $Rh_6(CO)_{16}$, [Rh (norbornadiene)$(PPh_3)_2]^+[PF_6]^-$, $[Rh(CO)_3(PPh_3)_2]^+[BPh_4]^-$, $RhCl(CO)(PEt_3)_2$, $[RhCl(cyclooctadiene)]_2$, $[Rh(CO)_3(PR_3)_2]^+BPh_4^-$, $[Rh(CO)_3(PR_3)_2]^+PF_6^-$, $HCo(CO)_4$, $Ru_3(CO)_{12}$, $[RuH(CO)(acetonitrile)_2(PPh_3)_3]^+[BF_4]^-$, $PtCl_2$(cyclooctadiene), $[Ir(CO)_3(PPh_3)]^+[PF_6]^-$, $[HPt(PEt_3)_3]^+[PF_6]$, where R is a hydrocarbyl radical, for example alkyl, cycloalkyl, aryl, which may or may not be substituted. Completely inorganic salts may also be used, such as $Rh_2O_3$, $Pd(NO_3)_2$ and $Rh(NO_3)_3$, also halides such as $RhCl_3$, $3H_2O$, although halides are not preferred. The transition metal compound and/or the ligand can also be already dissolved in an organic solvent.

The catalytic compound is obtained by mixing the liquid salt with the transition metal compound and possibly the ligand, in any manner.

Transition metal-organic ligand catalytic complexes can be prepared remote from the reaction medium and introduced thereto for reaction. They can also be formed in situ in the reaction medium, by introducing the components required for their formation.

A further advantage of the process of the present invention is that a very wide variety of ligands can be used which are not compatible with water but which are stable in these media, such as phosphites which are extremely hydrolysable. Thus synthesis is much simpler than that of phosphines.

In general, the catalytic composition can contain an organic solvent which is miscible or partially miscible such as an aromatic hydrocarbon, and/or a non miscible aliphatic hydrocarbon which can better separate the phases. Preferably, the catalytic composition does not contain water.

The concentration of the transition metal compound (preferably a complex) in the "molten salt" is not critical. It is advantageously in the range 1 mmole of compound per liter of "molten salt" to 500 mmoles per liter, preferably in the range 2 to 200 mmoles per liter, and more preferably in the range 2 to 100, still more preferably 2 to 50. The molar ratio between the organic ligand and the transition metal compound can be in the range 1 to 100, preferably in the range 1 to 20.

The components of the composition of the invention can be mixed in any order at a temperature in the range $-20°$ C. to $+200°$ C., advantageously in the range $-20°$ C. and less than 90° C., and preferably 30° C. to less than 150° C., advantageously 0° C. to less than 150° C., 0° C. to 120° C., or 0 to less than 90° C., preferably 0° C. to 85° C. or 0° C. to 50° C.

Olefinically unsaturated compounds which can be hydroformylated in accordance with the invention are monoolefins, diolefins and in particular conjugated diolefins, compounds containing one or more heteroatoms, in particular unsaturated compounds such as a ketone or carboxylic acid function. An example is the hydroformylation of ethylene to propionaldehyde, propylene to butyraldehyde and isobutylraldehyde, butene to pentanal and isopentanals, pentene to hexanal and isohexanals, hexenes to isoheptanals, isooctenes to isonanals, butadiene to adipaldehyde or the hydroformylation of octenes and pentadienes. These compounds can be used pure or diluted with saturated or unsaturated hydrocarbons.

The ratio of the partial pressures of carbon monoxide to hydrogen in the hydroformylation reaction medium can be from 1:10 to 10:1, preferably a ratio of 1:1, but any other ratio can be used when carrying out the process.

The temperature at which hydroformylation is carried out is in the range 30° C. to 200° C. Advantageously, the temperature is below 150° C., preferably between 50° C. and less than 150° C. and more preferably less than 90° C., more advantageously at most 85° C. A preferred temperature range is between 50° C. and less than 150° C., more advantageously 30° C. to 120° C., still more preferably 30° C. to less than 90° C. The pressure can be in the range 1 MPa to 20 MPa, preferably in the range 2 MPa to 10 MPa.

The catalytic unsaturated compound hydroformylation reaction can be carried out in a batch, semi-continuous or continuous system in one or more reaction stages. At the reactor outlet, the organic phase containing the reaction products (aldehydes) is advantageously separated by simply decanting the catalytic polar phase containing the "molten salt" and the major portion of the catalyst. The polar phase which contains at least part of the catalyst is at least partially returned to the reactor, the other portion being treated to eliminate catalyst residues.

The following examples illustrate the invention without limiting its scope:

EXAMPLE 1

4 ml of butylmethylimidazolium hexafluorophosphate, 19.3 mg (0.075 mmole) of $Rh(acetylacetonate)(CO)_2$ complex and 186 mg (0.71 mmole) of triphenylphosphine dissolved in 2 ml of toluene, 2 ml of heptane (standard) and 7.5 ml (68 mmole) of 1-pentene were introduced at ambient temperature into a 100 ml stainless steel double envelope reactor which had been purged of air and humidity and contained a mixture (1:1 mol/mol) of hydrogen-carbon monoxide at atmospheric pressure. The pressure of the hydrogen-carbon monoxide mixture was raised to 2 MPa and the temperature was raised to 82° C. and stirring was commenced. After 2 hours, stirring was stopped and the mixture was allowed to settle out; the upper organic phase was extracted; it was very slightly coloured. More than 99% of the 1-pentene had been converted. The hexenal yield was 75 mole % and that of 2-methylpentenal was 24%. The remainder (1%) was constituted by 2-pentene and pentane.

EXAMPLE 2

7.5 ml of 1-pentene and 2 ml of heptane were added to the ionic phase from the preceding example, from which the organic phase had been removed. This mixture was placed in a hydrogen-carbon monoxide mixture under the same conditions the preceding example. After 2 hours of reaction, more than 99% of the 1-pentene had been converted and the product distribution was practically identical to that of Example 1.

EXAMPLE 3

The apparatus described in Example 1 was used. 4 ml of liquid ethylmethylimidazolium tetrafluoroborate, 0.5 ml of water, 19.3 mg (0.075 mmole) of Rh(acetylacetonate)(CO)$_2$ complex, 0.71 mmole of the sodium salt of trisulphonated triphenylphosphine, 2 ml of heptane (standard) and 7.5 ml (68 mmole) of 1-pentene were introduced at ambient temperature. This was placed under a pressure of 4 MPa of carbon monoxide-hydrogen mixture and the temperature was raised to 80° C. After 2 hours of reaction, the organic phase, which was completely colourless, was decanted off. 33% of the 1-pentene had been converted, and the aldehyde selectivity was more than 99%.

EXAMPLE 4

The apparatus described in Example 1 was used. 4 ml of liquid ethylmethylimidazolium tetrafluoroborate, 0.5 ml of water, 0.075 mmole of PtCl$_2$(cyclooctadiene) complex, 0.71 mmole of the sodium salt of trisulphonated triphenylphosphine, 2 ml of heptane (standard) and 7.5 ml (68 mmole) of 1-pentene were introduced. This was placed under a pressure of 4 MPa of carbon monoxide-hydrogen mixture and the temperature was raised to 80° C. After 2 hours of reaction, the organic phase, which was completely colourless, was decanted off. More than 25% of the 1-pentene had been converted, and the aldehyde selectivity was more than 99%.

EXAMPLE 5

The apparatus described in Example 1 was used. 4 ml of ethylmethylimidazolium tetrafluoroborate, 0.5 ml of water, 0.075 mmole of [RuH(CO)(acetonitrile)$_2$(PPh$_3$)$_3$]$^+$[BF$_4$]$^-$ complex, 2 ml of heptane (standard) and 7.5 ml (68 mmole) of 1-pentene were introduced. This was placed under a pressure of 4 MPa of carbon monoxide-hydrogen mixture and the temperature was raised to 80° C. After 2 hours of reaction, the organic phase, which was completely colourless, was decanted off. More than 25% of the 1-pentene had been converted, and the aldehyde selectivity was more than 99%.

Thus the process of the invention, in addition to the advantage of being able to carry out the reaction at temperatures which are lower than those of the prior art if desired, can produce aldehydes with high selectivity (at least 40% or better, at least 50% and more generally 70% or even 80% or 85%).

The fact that the molten salt is liquid at temperatures which are close to ambient temperature or even lower facilitates the process, as handling solids such as those in the prior art renders these processes more difficult to operate.

The preceding examples can be repeated with similar success by substituting the generically or specifically described reactants and;or operating conditions of this invention for those used in the preceding examples.

The entire disclosure of all applications, patents and publications, cited above and below, and of corresponding French application 95/14.147, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process in a reactor for conducting a liquid phase hydroformylation of at least one olefinically unsaturated compound by carbon monoxide and hydrogen in the presence of a catalytic composition containing at least one transition metal compound and at least one organic-inorganic salt which does not contain tin or germanium, the process being characterized in that said salt is a quaternary ammonium and/or phosphonium salt with general formula Q$^+$A$^-$, where Q$^+$ represents quaternary ammonium and/or phosphonium and A$^-$ an anion, in that said salt is a liquid solvent for the transition metal compound at a temperature below 90° C., and said hydroformylation is conducted at below 90° C., and wherein anion A$^-$ is tetrafluoroborate providing that Q$^+$ represent quaternary ammonium or anion A$^-$ is selected from the group consisting of hexafluorophosphate, hexafluoroantimonate, hexafluoroarsenate, fluorosulphonate, bis-perfluoroalkylsulphonyl amides, perfluoroalkyl sulphonates, dichlorocuprate, tetrachloroborate, tetrachloroaluminate, and trichlorozincate.

2. A process according to claim 1, in which the quaternary ammonium and/or phosphonium cation is selected from the group consisting of

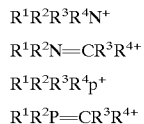

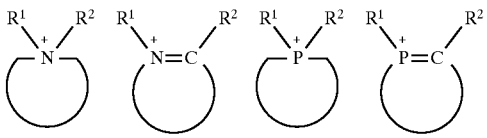

where R$^1$, R$^2$, R$^3$ and R$^4$, which may be identical or different, represent hydrogen with the exception of NH$_4^+$, and hydrocarbyl residues containing 1 to 12 carbon atoms, and in which the rings are constituted by 4 to 10 atoms.

3. A process according to claim 1, in which the quaternary ammonium and/or phosphonium cations have the general formulae:

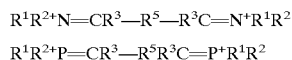

where R$^1$, R$^2$, R$^3$, which may be identical or different, represent hydrogen or hydrocarbyl residues containing 1 to 12 carbon atoms, and R$^5$ represents an alkylene or phenylene residue.

4. A process according to claim 1, in which the quaternary ammonium and/or phosphonium cations are selected from the group consisting of N-butylpyridinium, N-ethylpyridinium, 3-butyl-1-methylimidazolium, diethylpyrazolium, 3-ethyl-1-methylimidazolium, pyridinium, trimethylphenylammonium, and tetrabutylphosphonium.

5. A process according to claim 1, in which the quaternary ammonium and/or phosphonium salts are selected from the group constituted by N-butylpyridinium hexafluorophosphate, N-ethylpyridinium tetrafluoroborate, tetrabutylphosphonium tetrafluoroborate, 3-butyl-1-methylimidazolium hexafluoroantimonate, 3-butyl-1-methylimidazolium hexafluorophosphate, 3-butyl-1-methylimidazolium trifluoromethylsulphonate, pyridinium fluorosulphonate, trimethylphenylammomium hexafluorophosphate, 3-butyl-1-methylimidazolium dichlorocuprate, pyridinium tetrachloroborate, 3-butyl-1-methylimidazolium tetrachloroaluminate, and 3-butyl-1-methylimidazolium trichlorozincate.

6. A process according to claim 1, in which the transition metal is cobalt, rhodium, iridium, ruthenium, palladium or platinum.

7. A process according to claim 1, in which the transition metal compound is a transition metal complex.

8. A process according to any one of the preceding claims, in which the catalytic composition also contains a ligand or a ligand associated with the transition metal compound, said ligand being selected from the group formed by tertiary phosphines, tertiary arsines, tertiary stibines and phosphites.

9. A process according to claim 1, in which the transition metal compound is selected from the group consisting of $HRh(CO)(PR_3)_3$, $HRh(CO)_2(PR_3)$, $HRh(CO)[P(OR)_3]_3$, $Rh(acac)(CO)_2$, (acac represents acetylaccetonate), $Rh_6(CO)_{16}$, $[Rh(CO)_3(PPh_3)_2]^+[BPh_4]^-$, $RhCl(CO)(PEt_3)_2$, $[RhCl(cyclooctadiene)]_2$, $[Rh(CO)_3(PR_3)_2]^+BPh_4^-$, $[Rh(CO)_3(PR_3)_2]^+PF_6^-$, $[Rh(norbornadiene)(PPh_3)_2]^+[PF_6]^-$, $HCo(CO)_4$, $Ru_3(CO)_{12}$, $[RuH(CO)(acetonitrile)_2(PPh_3)_3]^+[BF_4]^-$, $PtCl_2(cyclooctadiene)$, $[Ir(CO)_3(PPh_3)]^+[PF_6]^-$, $[HPt(PEt_3)_3]^+[PF_6]$, $Rh_2O_3$, $Pd(NO_3)_2$ and $Rh(NO_3)_3$, where R is a hydrocarbyl radical, which may or may not be substituted.

10. A process according to claim 8, in which the ligand contains at least one amine, ammonium, alcohol, carboxylic acid or sulphonate function.

11. A process according to claim 1, in which the catalytic composition contains a ligand or a ligand associated with a transition metal compound, selected from the group formed by triphenylphosphine, triphenylphosphite, triethylphosphite, the sodium salt of monosulphonated triphenylphosphine, and the sodium salt of trisulphonated triphenylphosphine.

12. A process according to claim 1, in which the concentration of the compound(s) of the transition metal(s) is 1 to 500 mmoles per liter with respect to the ammonium and/or phosphonium salt.

13. A process according to claim 1, in which the catalytic composition also contains an organic solvent.

14. A process according to claim 13, in which the solvent is selected from the group consisting of aromatic hydrocarbons and aliphatic hydrocarbons.

15. A process according to claim 1, in which the olefinically unsaturated compound is selected from the group consisting of monoolefins, diolefins, conjugated diolefins, and compound containing one or more unsaturated heteroatoms.

16. A process according to claim 15, in which the monoolefin is selected from the group formed by ethylene, propylene, butene, pentene, hexenes and octenes and the diolefin is selected from the group formed by butadiene and the pentadienes.

17. A process according to any one of claims 7 to 14, in which the olefinically unsaturated compound is a compound carrying a ketone function or a carboxylic acid function.

18. A process according to claim 1, in which an organic phase containing the reaction products is separated from the polar phase, said polar phase containing at least a portion of the catalyst being at least partially recycled to the hydroformylation reactor.

19. A process according to any one of claim 1, operating between 30° C. and 90° C., at a total pressure in the range 1 MPa to 20 MPa, the ratios of the partial pressure of carbon monoxide to hydrogen being 1:10 to 10:1.

20. A process according to claim 1, in which the aldehydes are selectively produced.

21. A process in a reactor for conducting a liquid phase hydroformylation of at least one olefinically unsaturated compound by carbon monoxide and hydrogen in the presence of a catalytic composition containing at least one transition metal compound and at least one organic-inorganic salt which does not contain tin or germanium, the process being characterized in that said salt is a quaternary ammonium and/or phosphonium salt with general formula $Q^+A^-$, where $Q^+$ represents quaternary ammonium and/or phosphonium and $A^-$ an anion, in that said salt is a liquid solvent for the transition metal compound at a temperature below 90° C., and said hydroformylation is conducted at below 90° C., and wherein anion $A^-$ is selected from the group consisting of hexafluorophosphate, hexafluoroantimonate, hexafluoroarsenate, fluorosulphonate, bis-perfluoroalkylsulphonyl amides, perfluoroalkyl sulphonates, dichlorocuprate, tetrachloroborate, tetrachloroaluminate, trichlorozincate, and when $Q^+$ is quaternary ammonium, tetrafluoroborate wherein the transition metal compound is other than a ruthenium compound.

22. A process in a reactor for conducting a liquid phase hydroformylation of at least one olefinically unsaturated compound by carbon monoxide and hydrogen in the presence of a catalytic composition containing at least one transition metal compound and at least one organic-inorganic salt which does not contain tin or germanium, the process being characterized in that said salt is a quaternary ammonium and/or phosphonium salt with general formula $Q^+A^-$, where $Q^+$ represents quaternary ammonium and/or phosphonium and $A^-$ an anion, in that said salt is a liquid solvent for the transition metal compound at a temperature below 90° C., and said hydroformylation is conducted at below 90° C., and wherein anion $A^-$ is selected from the group consisting of hexafluorophosphate, hexafluoroantimonate, hexafluoroarsenate, fluorosulphonate, bis-perfluoroalkylsulphonyl amides, perfluoroalkyl sulphonates, dichlorocuprate, tetrachloroborate, tetrachloroaluminate, and trichlorozincate.

23. A process according to claim 21, wherein $A^-$ is other than tetrafluoroborate.

24. A process according to claim 1, wherein the salt is liquid at below 50° C.

25. A process according to claim 1, conducted under conditions so as to achieve an aldehyde selectivity of at least 40%.

26. A process according to claim 1, conducted under conditions so as to achieve an aldehyde selectivity of at least 50%.

27. A process according to claim 1, conducted under conditions so as to achieve an aldehyde selectivity of at least 70%.

28. A process according to claim 1, further comprising withdrawing a hydroformylation reaction effluent from said reactor, said reaction effluent comprising: (a) an organic phase containing reaction products and (b) a catalytic polar phase containing said salt and the major portion of the catalyst; decanting said catalytic polar phase from said organic phase; and recycling at least part of said polar phase to the reactor.

* * * * *